United States Patent
DeLise, Jr. et al.

(10) Patent No.: US 9,008,411 B2
(45) Date of Patent: Apr. 14, 2015

(54) METHOD, SYSTEM, AND APPARATUS FOR IDENTIFYING PHARMACEUTICAL PRODUCTS

(75) Inventors: Stephen W. DeLise, Jr., West Islip, NY (US); James F. DeLise, Babylon, NY (US); Frank DeLise, Smithtown, NY (US)

(73) Assignee: MiniGraphics, Inc., Hauppauge, NY (US)

( * ) Notice: Subject to any disclaimer, the term of this patent is extended or adjusted under 35 U.S.C. 154(b) by 1010 days.

(21) Appl. No.: 13/103,285

(22) Filed: May 9, 2011

(65) Prior Publication Data

US 2012/0290619 A1    Nov. 15, 2012

(51) Int. Cl.
*G06K 9/00* (2006.01)
*G06F 19/00* (2011.01)

(52) U.S. Cl.
CPC .......... *G06K 9/00671* (2013.01); *G06F 19/326* (2013.01); *G06F 19/3456* (2013.01)

(58) Field of Classification Search
USPC ......... 382/100, 103, 154, 181, 190, 195, 203, 382/285; 707/609–686; 348/92, 135, 348/169–172
See application file for complete search history.

(56) References Cited

U.S. PATENT DOCUMENTS

| | | | |
|---|---|---|---|
| 5,845,264 A | 12/1998 | Nellhaus | |
| 6,535,637 B1 * | 3/2003 | Wootton et al. | 382/190 |
| 6,543,692 B1 | 4/2003 | Nellhaus et al. | |
| 7,019,743 B1 | 3/2006 | Wainwright et al. | |
| 7,059,526 B1 | 6/2006 | Sullivan et al. | |
| 7,136,539 B2 | 11/2006 | Weyl | |
| 7,218,395 B2 * | 5/2007 | Kaye et al. | 356/301 |
| 7,712,665 B2 | 5/2010 | Ortiz et al. | |
| 8,417,539 B2 * | 4/2013 | Chapman et al. | 705/2 |
| 2003/0216831 A1 * | 11/2003 | Hart et al. | 700/235 |
| 2006/0226234 A1 | 10/2006 | Kettinger et al. | |
| 2007/0026064 A1 | 2/2007 | Yoder et al. | |
| 2007/0265880 A1 | 11/2007 | Bartfeld et al. | |
| 2008/0000979 A1 | 1/2008 | Poisner | |
| 2009/0080735 A1 * | 3/2009 | Chapman et al. | 382/128 |
| 2009/0154764 A1 * | 6/2009 | Khan et al. | 382/100 |
| 2010/0091285 A1 | 4/2010 | Newcomb | |
| 2011/0091068 A1 * | 4/2011 | Stuck et al. | 382/103 |
| 2012/0084091 A1 * | 4/2012 | Hanina et al. | 705/2 |
| 2013/0194414 A1 * | 8/2013 | Poirier et al. | 348/92 |

OTHER PUBLICATIONS

"Pill Identification Wizard," Drugs.com, http://www.drugs.com/pill_identification_drug_picture.html, accessed May 9, 2011.
"The Pill Phone," https://www.pillphone.com/PillLogin.htm (1 of 2), accessed May 9, 2011.
"From 2D to 3D," http://www.looxis.com, accessed May 9, 2011.

(Continued)

*Primary Examiner* — Anand Bhatnagar
(74) *Attorney, Agent, or Firm* — Keusey & Associates, P.C.

(57) ABSTRACT

A method, system and apparatus is provided for identifying pharmaceutical products. A database of known pharmaceuticals is provided with links to virtual 3D models of each pharmaceutical. When a pill needs to be identified, an image of the pill is transmitted to the database CPU. The CPU screens out non-matching records and obtains perspective data based on the orientation of the pill. The CPU manipulates a 3D model into the same perspective as the pill to facilitate identification.

17 Claims, 5 Drawing Sheets

(56) References Cited

OTHER PUBLICATIONS

"Pillbox vs. Pillboxer vs. The Pill Phone," Mobi Health News, http://mobihealthnews.com, accessed May 9, 2011.

Hartl, Andreas et al. "Computer-Vision Based Pharmaceutical Pill Recognition on Mobile Phones," Proceedings of CESCG 2010: The 14th Central European Seminar on Computer Graphics, May 10, 2010.

Schmalstieg, Dieter et al. "Experiences With Handheld Augmented Reality," 6th IEEE and ACM International Symposium, Nov. 13, 2007.

Suzuki, Motofumi T. et al. "A 3D Model Retrieval System for Cellular Phones," IEEE International Conference on Systems, Man, and Cybernetics, Oct. 5, 2003.

International Preliminary Examination Report, dated Nov. 21, 2013, from International Application No. PCT/US2012/036715.

Written Opinion, dated Nov. 21, 2013, from International Application No. PCT/US2012/036715.

\* cited by examiner

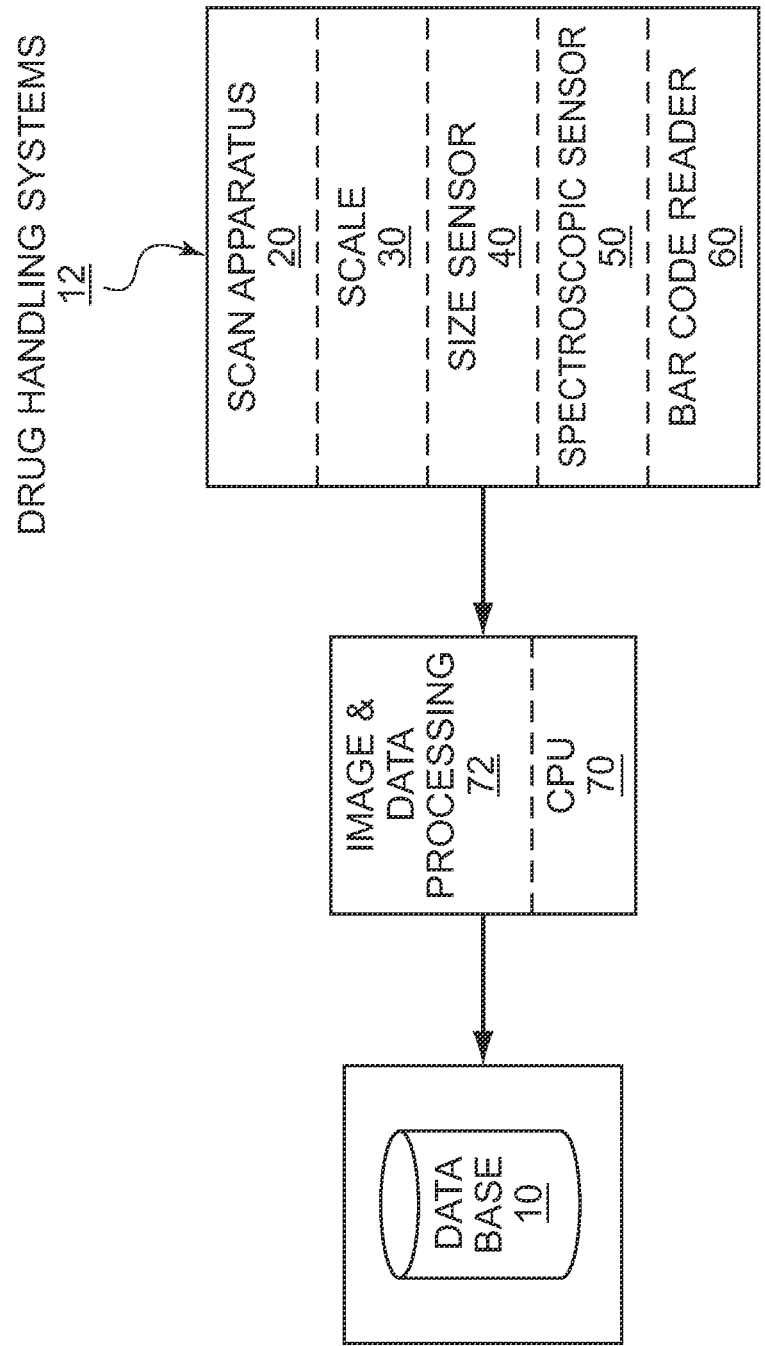
FIG. 1 – *Prior Art*

US 9,008,411 B2

METHOD, SYSTEM, AND APPARATUS FOR IDENTIFYING PHARMACEUTICAL PRODUCTS

BACKGROUND OF THE INVENTION

1. Field of the Invention

The invention relates to a method, system and apparatus for identifying pharmaceutical products.

2. The Prior Art

There are numerous instances where the identification of a certain pharmaceutical is required. On the dispensing side physicians, hospitals, retirement homes and drug stores need a day to day reference guide. In the field, there is a need for law enforcement, EMTs and others to be able to identify a pill in connection with an investigation or a sick individual.

The Physician's Desk Reference (PDR) is a book which contains photos and corresponding descriptions of available pharmaceuticals. The book format is limited because each year physicians must obtain a new copy in order to have an up to date listing. Typically, the PDR is not available in the field when law enforcement or EMTs locate pills at a scene.

To address the problem of field identification of pharmaceuticals, several systems have been proposed that incorporate a database of known pharmaceuticals. The database is typically an electronic version of the PDR, in that is contains photos and corresponding descriptions of pharmaceuticals in a searchable format. One example is the Pill Identification Wizard at www.drugs.com.

The Pill Book is a printed consumer guide to pharmaceuticals containing photos and corresponding descriptions. Certain mobile apps have been developed to search through an electronic version of The Pill Book or other databases. An "app" is an abbreviation for a computer application, frequently referring to applications which can be deployed on mobile devices. One such app is called The Pill Phone, which is described at www.pillphone.com. The Pill Phone app includes a pill lookup feature, where three or more letters are used to perform an alphabetic search for matching pill imprints. Another app called myCommunity Pillbox lets users connect to another medication database. A further app called Pillboxer allows users to search through a different database of medications.

In order to identify a pill, the following references use various coding schemes to mark the pill. When properly read, the code can be used to directly access the corresponding record in the database. U.S. Pat. No. 5,845,264 places a bar code on each pill. A scanner connected to a computer reads the bar code and then accesses a record from the database stored on the computer's hard drive. U.S. Pat. No. 6,543,692 places a common visual symbol on each pill in conjunction with a matrix type bar code. The common visual symbol can communicate to an EMT the category of the pharmaceutical. A code reading device can determine the type of pharmaceutical by reading the bar code. U.S. Pat. No. 7,059,526 uses bar codes printed on the pills to manage hospital inventory. In U.S. Patent Application Publication 2006/02226234 a bar code or a 2D data matrix bar code is printed or etched on a debossed region of the surface of the pill. In U.S. Patent Application Publication 2007/0026064 a holographic mark or watermark applied to the pill. U.S. Pat. No. 7,712,665 uses a color differentiated bar code marking on the pill. The marking is read by a proprietary scanner and may communicate over the interne to access the pharmaceutical database.

All of the above pill coding solutions have major drawbacks. The success of such a system requires all pharmaceutical companies and regulatory authorities to agree on a coding format, which will add to the cost of production. In addition, most systems require a scanner or computer thereby limiting its effectiveness as a field deployable tool. In addition, even if one of the above systems was universally implemented, it would not be effective in identifying older pills that do not have the bar code. To address these concerns, the following proposals seek to provide pharmaceutical identification by capturing pill images under controlled conditions with scanning stations.

In U.S. Patent Application Publication 2009/0080735 a method is disclosed for scanning pharmaceutical pills within a vial. The vial is placed in a scanning device having two different light sources. Under the first light source, a first spectral signature of the vial is captured. Then under the second light source, a second spectral signature is captured. The two spectral signatures are processed and compared to shapes stored in the pharmaceutical database.

In U.S. Patent Application Publication 2010/0091285 a method is disclosed for scanning pharmaceuticals pills within a vial. The vial is placed in a scanning station which illuminates the vial with a light color that is the inverse of the color of the vial. Alternatively, the vial is illuminated with electromagnetic radiation outside the visible range. The illumination wavelength is chosen to produce an image of the pill with the container being canceled out.

In U.S. Pat. No. 7,218,395 a vial of pharmaceuticals is placed on a sensor bed. A laser diode is used to excite Raman-active modes in the pharmaceutical to obtain a Raman spectral signature. That signature is compared to a database containing Raman spectral signatures of known pharmaceuticals. The system also weighs the vial and uses known weights to confirm that the vial contains the correct number of pills.

In U.S. Pat. No. 7,136,539 an imaging staging module is used to capture images of the pharmaceutical from at least two different visual perspectives. The weight of the pill is also obtained. The images and weight are compared to a database of known pills.

In U.S. Patent Application Publication 2008/0000979 a mechanical device is provided to roll a pill along various axes while an optical device records images of the pill. An infrared or near-infrared analytical tool may also be used to detect a composition of the pill. The images and composition data is then compared to a database of known pills.

These scanning stations are impractical for field use. Accordingly, it would be desirable to provide a more streamlined system where simple pill images can be captured and transmitted to a system where image processing can be combined with the pharmaceutical database contents to quickly and reliably identify pills.

SUMMARY OF THE INVENTION

Therefore, it is an object of an embodiment of the present invention to process a simple image of a pill and identify the corresponding known pharmaceutical.

It is a further object to allow field personnel to transmit simple pill images over a wireless telecommunications link to a central processing facility.

It is another object to provide each database record with a virtual 3D model of the pharmaceutical.

It is a further object to provide comparison algorithms to match the 2D field image with a corresponding 2D rendering of a perspective-adjusted 3D model from the database.

These and other related objects according to the invention are achieved by a method and system for identifying a pill. The method begins with the step of storing a pharmaceutical database on an electronic storage device including a virtual 3D model of each pharmaceutical within the database. Then transmitting a simple 2D image of a pill to a central processing unit (CPU) that is operatively coupled to the pharmaceutical database. The perspective of the 2D image is determined, which may be referred to as the first perspective or the query perspective. An image of the virtual 3D model is generated from a [second] perspective that matches the [first] perspective of the 2D image.

The pharmaceutical database includes records of known pharmaceuticals with each record containing (i) a virtual 3D model, (ii) static characteristics, for example, color, shape and alphanumeric characters of the pharmaceutical, and (iii) medical and safety data. The simple 2D image comprises an image taken at a remote field location under ambient lighting conditions with a commercially available digital camera in the absence of spectrally modified lighting other than the camera's flash.

The transmitting step further includes transmitting a simple 2D query image via a wireless cellular telephone network to the CPU, wherein the CPU contains a set of instructions for performing data and image processing, and comparing functions. Prior to said generating step, the method further includes analyzing the simple 2D image to identify one of the color, shape or alphanumeric characters of the imaged pill, wherein the simple 2D image comprises a 2D query image. Prior to said comparing step, the method further includes comparing one of the analyzed color, shape or alphanumeric characters to the static characteristics in the database to divide the records into a no-match group and a matched group, whereby only records in the matched group will be eligible for the generating step.

The generating step includes retrieving a virtual 3D model from a record in the matched group and generating a perspective-adjusted 3D model. The generating step further includes rendering a 2D matching image of the perspective-adjusted 3D model and comparing the 2D matching image to the 2D query image. Following said generating and comparing steps, the method includes identifying the pill as a known pharmaceutical and transmitting medical and safety data for that pharmaceutical back to the source of the query.

In an alternate embodiment there is provided a system for identifying a pill including an electronic storage device containing a pharmaceutical database including a virtual 3D model of each pharmaceutical in the database. A central processing unit (CPU) is operatively coupled to the electronic storage device. A set of instructions is provided for programming the CPU to perform data and image processing in response to a database query. An image generating module generates an image of a 3D model, wherein the selection of the 3D model is based on said data processing results and the image type is based on said image processing result.

A simple query image of a pill requiring identification is transmitted via a telecommunications network to the CPU. The pharmaceutical database includes a plurality of records of known pharmaceuticals. Each record contains (i) a link to a virtual 3D model, (ii) static characteristics, for example, color, shape and alphanumeric characters of the pharmaceutical, and (iii) medical and safety data. The image generating module contains a set of instructions for manipulating the 3D model which is capable of showing the 3D model in any orientation and at a range of scales.

The CPU obtains perspective and scale data from the query image and the image generating module orients the 3D model based on the perspective data to obtain the same perspective as the query image, wherein the oriented 3D model is defined as a perspective-adjusted 3D model. The perspective data from the query image is recorded via a coordinate system and transferred to the 3D model. The scale data is obtained from a reference object in the query image. The system further includes a reference library coupled to the image generating module, wherein the reference library contains 3D models of common objects used to scale the perspective-adjusted 3D model.

BRIEF DESCRIPTION OF THE DRAWINGS

The advantages, nature, and various additional features of the invention will appear more fully upon consideration of the illustrative embodiments now to be described in detail in connection with accompanying drawings. In the drawings wherein like reference numerals denote similar components throughout the views:

FIG. 1 is a schematic diagram of pharmaceutical identification systems according to the Prior Art.

DETAILED DESCRIPTION OF THE PREFERRED EMBODIMENTS

Figure 2A:
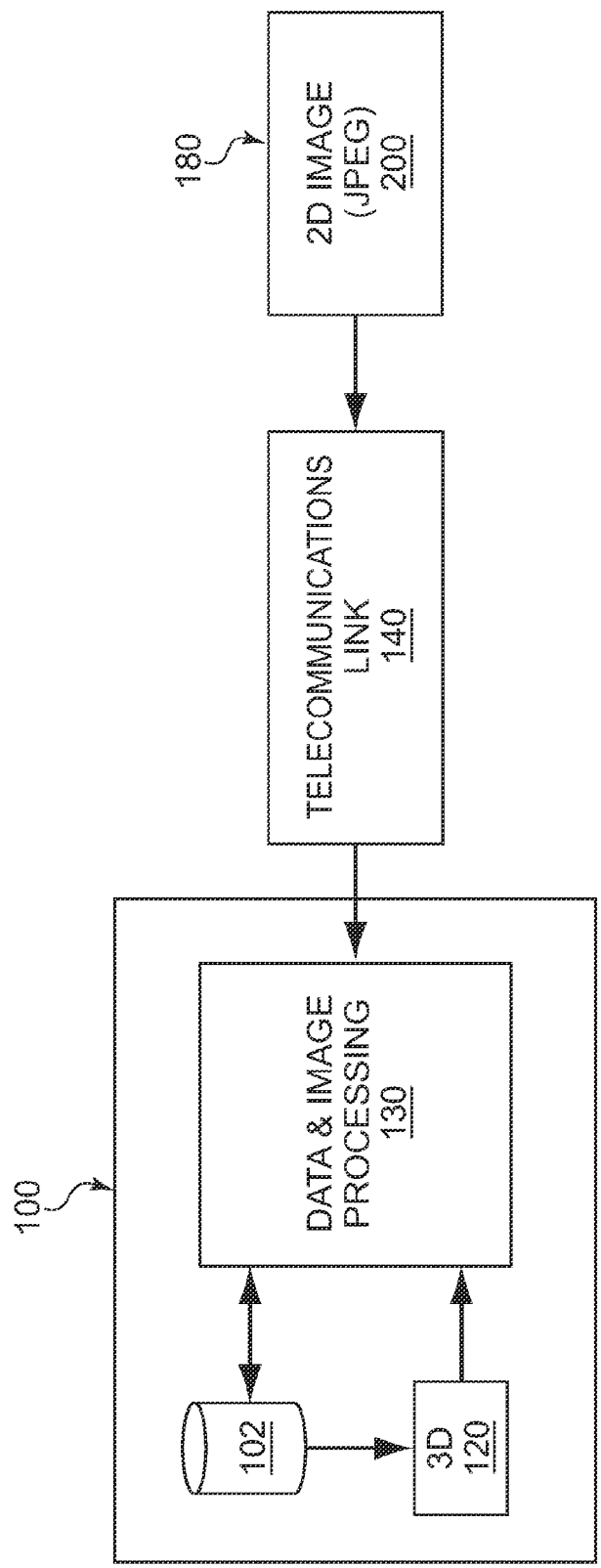
FIG. 2A is a schematic diagram of various hardware components used in an embodiment of the invention.

Referring now in detail to the drawings and in particular FIG. 1, there is shown a schematic diagram of a pharmaceutical identification system according to the prior art. The schematic is a general representative of the prior art systems shown, for example, in U.S. Pat. No. 7,136,539 FIG. 1, U.S. Pat. No. 7,218,395 FIG. 1 and U.S. Published Patent Application 2008/0000979 FIG. 2. A database 10 contains characteristics of known pharmaceuticals. A drug handling system 12 is provided in a pharmacy or hospital or retirement home. The drug handling system may take the form of a scan apparatus 20, a scale 30, a size sensor 40, a spectroscopic sensor 50 or a bar code reader 60. These drug handling systems are connected to a general purpose computer, depicted here as CPU 70. In certain cases the connections and the software needed to support the particular drug handling system is proprietary. The information collected from the drug handling system 12 is subject to image and or other forms of data processing in module 72. The purpose of module 72 is to manipulate the collected data into the same standard format that is used in database 10. A comparison is then performed between the manipulated data and the stored data.

A severe limitation is present with these drug handling systems 12 in that they are not field deployable. In order for these systems to function, images of the pills have to be captured under controlled conditions. For example, the pill has to be illuminated from certain angles, or with certain wavelengths of light and then the reflected light captured by a particular sensor or camera. The success of these systems is based on collecting data from the pill in the exact same manner as the data that is stored in the database.

In this specification the word "pill" is used as an informal term referring to the medication that needs to be identified. The word "pharmaceutical" refers to the medications contained within the system's database. Pill and pharmaceutical are meant to encompass both the singular and plural, and to include pills, tablets, suppositories, capsules and other physical forms of medication.

Turning now to FIG. 2A, there is shown a schematic diagram of an embodiment of the hardware or apparatus aspect according to the invention. As an overview, a central processing unit 100 CPU is provided which can be accessed by many users. Data from a remote field location 180 may be sent in to CPU 100 via a telecommunications link 140. As occurs many times a day, police or EMTs are called for assistance and find pills at the scene. A cell phone is used to take a photo of the pill, e.g. in jpg format. The photo is emailed via telecommunications link 140 to CPU 100. For example, a state or county may set up a single CPU 100 at a police station or in conjunction with a poison control center. All state or county agencies can then request pharmaceutical identification from the main CPU center.

When the 2D image 200 is received at CPU 100, a screening protocol is implemented to eliminate from consideration all records which are non-matching. A Data and Image Processing Unit 130 scans the 2D image 200 to extract the static characteristics, namely, color shape and alphanumeric characters. Next, Data and Image Processing Unit 130 determines the perspective of the 2D image. The virtual 3D models 120 of the matching records are image processed 130 to generate one or more images that match the perspective of the 2D image 200. The generated images are compared to the 2D image and a match or best match is identified. The drug information related to that pharmaceutical is then retrieved and sent to the remote field location 180, e.g. as a text message to the cell phone which originally sent the 2D image 200.

Database 102 includes a plurality of records. Each record contains fields and data corresponding to one known pharmaceutical. The record includes fields for the pills color, the pills shape, the alphanumeric characters and any design elements present on the pills. The alphanumeric characters and designs are frequently referred to as an imprint. For many tablets, the characters and designs are formed as an indentation in the face of the tablet. In other instances, the alphanumeric characters and designs are printed on the gelatin capsule. In this specification we use the terms alphanumeric character(s) and design(s) to encompass the term imprint(s). Collectively, these data items are defined as static characteristics. Score marks or edge bevels may be considered as imprints or as static characteristics. The CPU 100 utilizes the static characteristics to perform a first comparison or screening function to eliminate from further consideration records which are no match for the pill that is the subject of the query. It should be noted that the system according to the invention can be used with pills that do not have bar codes or other machine readable indicia.

The record further includes fields for the pharmaceutical manufacturer, drug interaction data, drug overdose data, and other medical and safety information. This medical and safety information is transmitted to the party in response to their query for pharmaceutical identification.

The record further includes a virtual 3D model of each pharmaceutical. For example, the virtual 3D model consists of an electronic representation of the pill which is generated from several still or scanned images. A modeling software application may be used such as SolidWorks or other CAD or product data management software. The 3D model may be generated by entering pill dimensions and expanding a 2D top view of the pill into a 3D model. The image processing module 130 analyzes the 2D image which comprises the query. It determines from which perspective the 2D query image was taken. The 3D model is then oriented to the same perspective and a 2D matching image is generated. Several matching images may be generated. The matching image is then compared to the query image to identify the pill. One or more matching images may be displayed to a user on a display device alongside the query image to allow the user to select the best match or confirm the CPU's selection of the best match. In an alternate embodiment, the 2D query image can be processed to form a 3D query model which can be compared with 3D models contained in database 102.

In a practical embodiment, one database of virtual 3D models may be provided to serve multiple CPU installations. The multiple CPUs can communicate with the 3D model database via a telecommunications link, for example, over a wide area network, local area network or the interne. In this configuration, the one 3D database can be easily updated with new drug information and updated modeling software. The CPU installations can subscribe to the 3D database and obtain proprietary software and secure access.

Figure 2B:
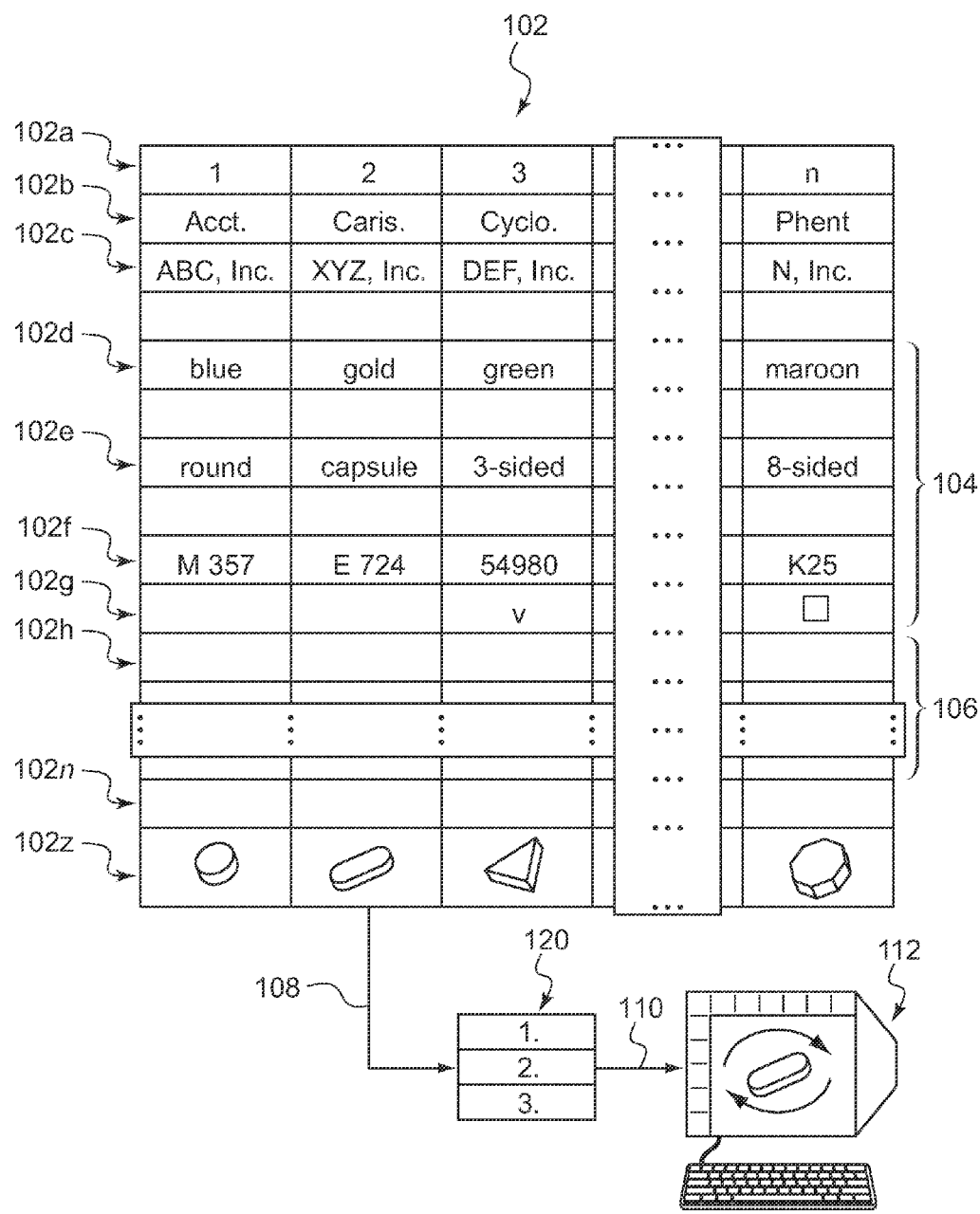
FIG. 2B is a diagram of an embodiment of a sample record from the pharmaceutical database according to the invention.

An exemplary format of the database 102 is shown in FIG. 2B. The columns represent records that are numbered in field 102a from 1 to n. Fields 102b provide the drug name. Fields 102c indicates the manufacturer. Fields 102d displays the color of the pharmaceutical. Fields 102e shows the pharmaceutical's shape. Field 102f indicates the imprint or alphanumeric characters. Field 102g illustrates any design on the pharmaceutical. We refer to fields 102d, 102e, 102f, and 102g as the static characteristics 104.

Other fields, not shown for the sake of clarity provide the dosage, drug class, pregnancy category, CSA schedule, availability, etc. Medical, safety and overdose information may be provided in fields 102h through 102n. Fields containing medical, safety and overdose information are collectively referred to as safety fields 106. Information in the safety fields will be sent to the party making the query once the pill has been identified.

Field 102z contains a 3D graphic and contains a link 108 to the 3D database 120. By clicking on a link, for example, the link in record 2, field 102z, the virtual 3D model is accessed and transferred via link 110 to open the virtual 3D file in a 3D software application 112. From the console running application 112, the virtual 3D model can be rotated, tilted, revolved and scale. The perspective from the query image is transferred, so that the 3D model is presented in the same perspective. The perspective-adjusted 3D model and then be used to generate a matching image. The perspective data from the query image may be recorded via a coordinate system and transferred to the 3D model. The matching image and the query image can be displayed side-by-side to confirm the identity of the pill.

The above hardware components may be used in combination with a telecommunications link, for example a local network, a wide area network, the interne, telephone lines and wired and wireless versions of same. The system may include a cellular telephone, PDA, PC, scanner or other device capable of capturing an image of the pill. In one embodiment of the invention, a cellular camera phone is used to take a picture of the pill and then wirelessly transmit the picture to the central processing unit.

The picture may be in a variety of electronic formats. An exemplary listing of formats includes JPEG (.jpg, .jpeg, .jpe), JPEG2000 (.jpr, .jpx, jp2, .j2k, .j2c, .jpc), GIF (.gif), PDF (.pdf), PNG (.png), PostScript (.ps), HTML (.html, .htm) and TIFF (.tiff, .tif). Other compressed or non-compressed formats may be used. Various video formats may be used such as Flash, mpg, mp4 or avi, where a still image can be captured from a single frame or frames. The key feature is the ability to transmit image data that can be processed by the CPU, and therefore other formats, or formats which will be developed in the future, can be utilized with the systems, methods and apparatus of the invention.

Figure 3A:
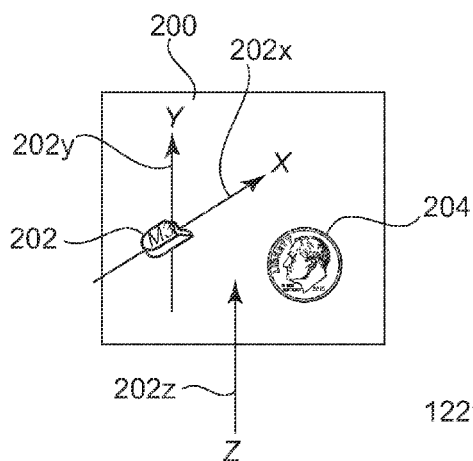
FIGS. 3A, 3B and 3C are a series of views illustrating the operation of the system according to the invention.

The apparatus from FIG. 2A and the database from FIG. 2B will now be described in conjunction with FIGS. 3A, 3B and 3C to provide a system configuration that achieves the purpose of pharmaceutical identification. In an embodiment of the invention there is provided a pharmaceutical database of known pharmaceuticals. The database is stored on an electronic storage device, such as a disc drive or other non-volatile memory device. The database is made up of records, where each record corresponds to one pharmaceutical. Each record has at least a first field containing static characteristics, a second field containing a virtual 3D image of the pharmaceutical, a third field containing manufacturer information, and a fourth field containing health and safety information. It should be understood that reference to a particular field means a field or multiple fields. The pharmaceutical database is operatively coupled to a CPU which contains a set of instructions for data and image processing.

At a remote location, an individual is interested in knowing the identity of a pharmaceutical. This pharmaceutical that is the subject of the query is referred to as the "pill." The individual takes a picture of the pill, typically with an electronic camera or a cellular camera phone. The image of the pill is transmitted to the CPU via a telecommunications link. In the case of a cellular camera phone, the image can be sent wirelessly as an email attachment to a phone number or email address coupled to the CPU.

The CPU performs data processing on the 2D image 200 of pill 202 using the static characteristics. From the 2D image 200 of pill 202, the CPU extracts the pill's color, the pill's shape, the alphanumeric characters and any design elements on the pill. As can be seen in FIG. 3A, the pill is a capsule shape, it has alphanumeric characters "M3" with other characters missing, and no visible design elements. Regarding color, the pill is a blue color. The CPU performs a comparison function on the database to eliminate from further consideration, any records which have static characteristics inconsistent with the pill's characteristics. For example, the database can be sorted by pill shape, with the capsule shapes being marked for the match bin, and all other being marked for the no-match bin. Then from the match bin, the records can be sorted by color, with only blue records being maintained in the match bin. The CPU can then eliminate from the match bin, any records which do not have both an M and a 3 in the alphanumeric field.

At this point several records with blue capsules and M and 3 field values will remain in the match bin. Next the CPU determines the perspective of the 2D image. In one embodiment, the CPU treats the pill as a point source and assigns an X alignment ray 202X and a Y alignment ray 202Y. In FIG. 3A, the X alignment is taken through the longitudinal width of the pill. The Y alignment is taken through the imprinted face of the pill. A Z distance 202Z is estimated, or if a reference object 204 is present, a measurement or relational distance can be obtained. The pill orientation may be obtained through edge detection techniques or algorithms, finite element mesh or modeling, image enhancement or image content extraction. The orientation may be defined by a coordinate system which can be directly transferred to the 3D model, or converted to an alternate system which can be applied to the 3D model.

Figure 3B:
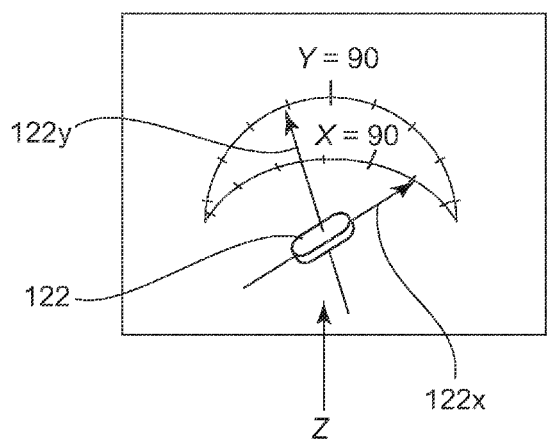

In FIG. 3B, the CPU opens the virtual image of the records in the match bin to access the 3D model 122. The 3D model is treated as a point disposed in the center of a longitude-latitude grid. The X alignment from the pill is transferred to a longitude 122X and latitude 122Y value. The longitude values 122X and latitude values 122Y can each range from 0 to 360 degrees. The ranges can be divided into 1 degree increments, or finer. The Y alignment can determine the degree of rotation about the X axis. In the case of a round pill, which has circular symmetry, one alignment can determine the angular elevation of the pills round face, with the second alignment being used to radially orient the pill's face. In an alternate scheme, a three axis system can be used, with each axis being assigned a longitude, latitude value.

Referring again to FIG. 3B, with the pill be oriented along the X and Y axes, the Z value can be used to pull or push the model into the page, to vary its size. A reference object 204 may be used to facilitate the scale or size adjustment. For example, the 3D modeling software may contain virtual 3D models of U.S. currency and coins which can be placed in their own longitude and latitude grid adjacent the pharmaceutical grid. The 3D models of currency and coins may be stored in a reference library.

Figure 3C:
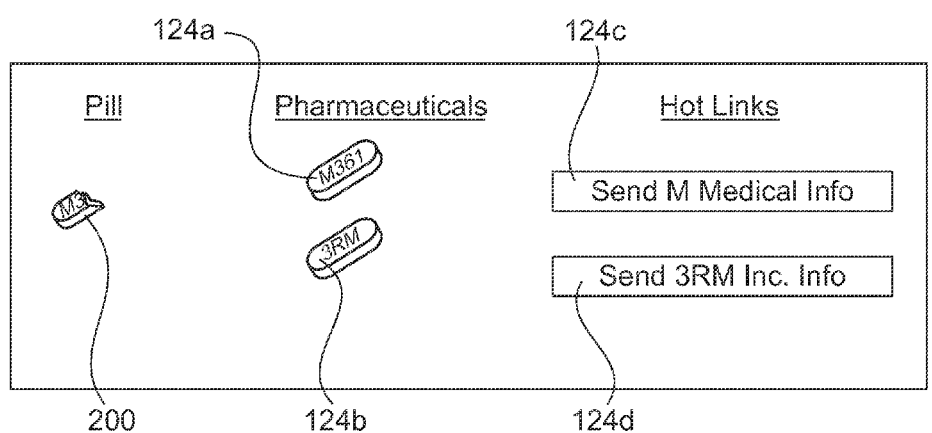

In FIG. 3C the pill image 200 is displayed next to one or more 2D images 124a, 124b of the perspective-adjusted 3D model. From FIG. 3A the system has determined the perspective of the 2D image. The characteristics of the 2D image were compared to the known characteristics to screen out non matches. From the matching group, an image was generated from the 3D model, by orienting the 3D model to the perspective of the 2D image. An operator or further image processing software can compare the original or cropped or enhanced 2D image 200 to one or more known pharmaceuticals. The system then provides for the corresponding medical or safety information 124c or 124d to be sent back to the individual making the inquiry.

Figure 4:
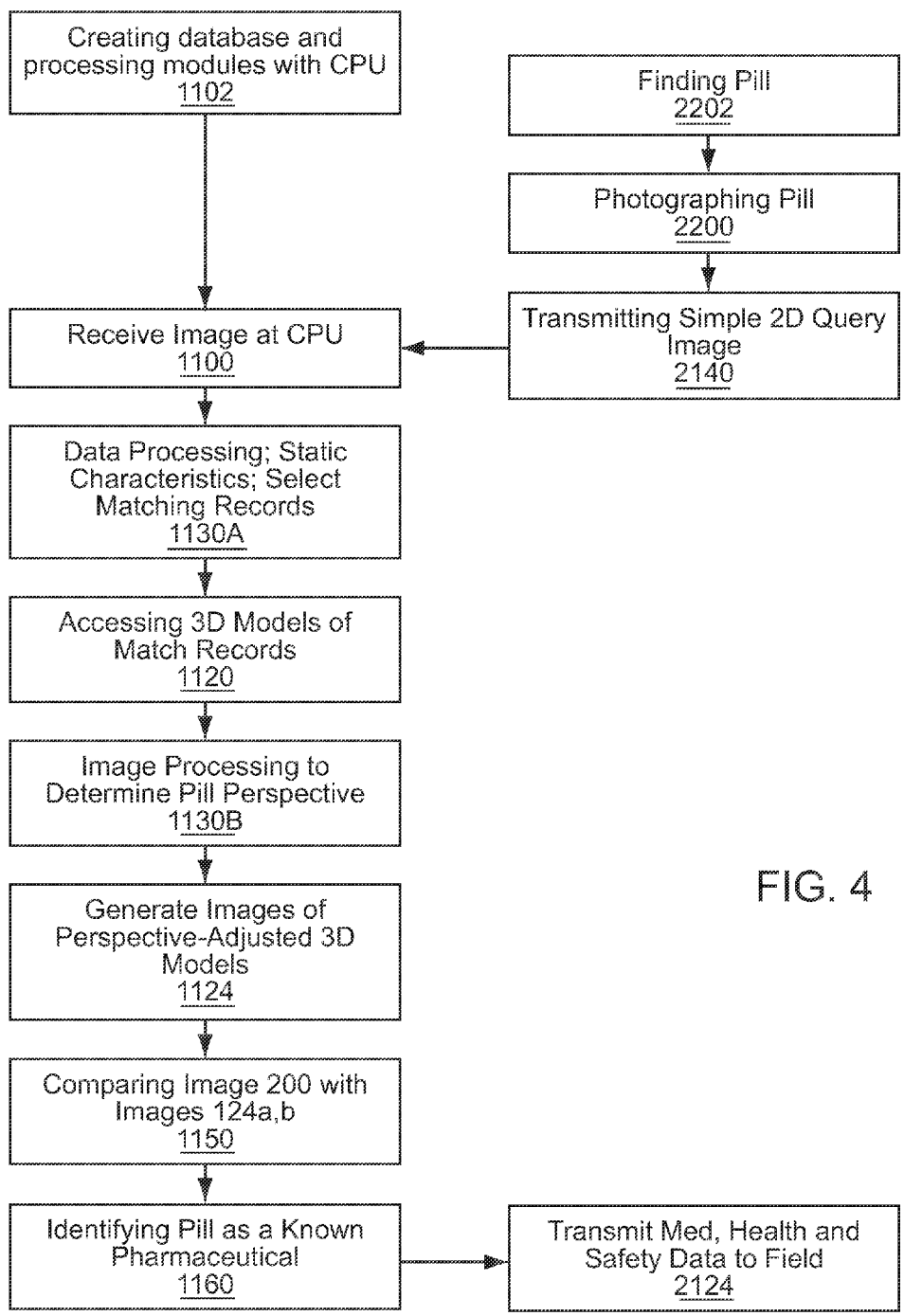
FIG. 4 is a flowchart showing the process of pill identification according to the invention.

From a method point of view, FIG. 4 shows a flowchart outlining various steps according to an embodiment of the invention to achieve the goal of pharmaceutical identification. In the flowchart, the column on the left with 1,000 prefixes, refers to steps performed at CPU 100, the so-called Local Steps. The column on the right with 2,000 prefixes refers to steps performed in connection with the pill's location, the so-called Field Steps.

In step 1102, a database is created with known pharmaceuticals. Each record has static characteristics, a corresponding virtual 3D model, and manufacturer, health and safety information.

In step 2202, a pill 202 is found which needs to be identified. Finding the pill 2202 may occur at a remote field location.

In step 2200, the pill is photographed. In Photographing the pill 2200, the method allows for commercially available digital cameras or cellular camera phones to transmit images. The method does not require any specialized or proprietary equipment. The photograph is referred to as a simple query image. The term "simple" means that the pill is photograph in the ambient lighting of the field. It is important to note that the pill need not be moved in order for the photograph to be taken. This could be important if paramedics arrive at an emergency and need to obtain a pill identification, but are not sure if the pill represents evidence. They may want to avoid touching the pill so that police investigators can collect fingerprints, etc.

In step 2140, the photograph is transmitted to CPU 100. In other words, this step involves Transmitting a simple 2D query image to the CPU. In step 1100, the photograph 200 is received at CPU 100. For speed and ease of access, the photograph can be sent via a wireless cellular telephone network.

The next step 1130A involves Data Processing of the received image using the Static Characteristics from the database to screen out no-match records and select a group of match records. From the match records, the method then involves Accessing 3D models of the Match Records in step

1120. In a separate processing step, Image Processing is performed 1130B to Determine the perspective of the pill within the query image.

Next, Generating Images of perspective-adjusted 3D models in step 1124. From the match records, the virtual 3D models are rotated into the perspective of the pill within the query image. This may comprise a one, two or three axis coordinate system orientation. The distance or scale is adjusted to give the 3D model the same size as the pill within the query image. Finally, jpg or other 2D images of the perspective-adjusted model are rendered.

These perspective-adjusted images are Compared in step 1150 to the 2D image of the pill. For example, Comparing Image 200 with generated image 124C from one record and image 124D from another record. Next, Identifying the pill as one of the pharmaceuticals is performed in step 1160. With the record now identified, Transmitting Medical, Health and Safety Data 124c to the field in step 2124 may proceed.

As described above in relation to step 1124 and 1150, the 3D model is adjusted for perspective and then rendered in 2D for comparison to the 2D query image. In an alternate embodiment, the 2D query image can be converted in to a 3D query image. For example, in step 1130A data processing of the 2D query image may include converting the 2D query image in to a 3D query image, utilizing a process analogous to the Looxis Faceworx service. In Faceworx, photos of faces are modeled to 3D by a 3D designer. According to the invention, the 2D query image can be modeled to 3D by software, for example, the 2D to 3D Conversion feature of SolidWorks. The 2D query image can be converted to an appropriate format, such as .dwg, for importing in to the SolidWorks converter. The front view can be defined as the surface containing the imprint. From the 3D database, the perspective-adjusted 3D model can be generated with the imprint side as the front view as a default to match the converted 3D query model.

As a result the process according to the invention can create the 3D query image quickly and automatically without human intervention. The pills are formed in a series of known sizes and shapes. Accordingly, the 2D to 3D conversion is a process with a fixed number of known outcomes or 3D models. In addition, pills have a degree of radial or geometric symmetry, so filling in missing segments is rather straightforward compared to modeling faces where each one contains a degree of uniqueness. After the 3D query image is created, it can be compared to a series of perspective-adjusted 3D models that have been selected following the matching records step 1130A. Therefore, the process according to FIG. 4 allows a 2D query image to be compared to a 2D image rendered from the perspective-adjusted model. The alternate process described in this paragraph, allows a 3D query image to be directly compared to the perspective-adjusted 3D model. In a further embodiment, a 2D to 2D comparison can be performed in addition to a 3D to 3D comparison to improve the accuracy of the comparing steps. The 2D to 2D comparison can be displayed to an operator side-by-side with the 3D to 3D comparison. Various comparison standards may be applied to the comparisons to give the operator an automatically generated grade, such as a probability of success rating. The probability of success rating can be applied to the 2D to 2D comparison, the 3D to 3D comparison or both.

As can be appreciated by those skilled in the art, the above described apparatus, system and method provide identification means for unknown pills. In the prior art systems, collection of information from the unknown pill must be conducted under carefully controlled conditions. In the invention, robust capabilities are provided to orient the virtual 3D model to match the perspective and scale of the unknown pill in the transmitted query image. Thus, the processing resources are shifted from the field to the central processor which is coupled to the database. The invention provides that the virtual 3D model can be manipulated to conform to the orientation of the pill shown in the query image. The background and other environmental factors can be adjusted, and lighting can be added to show shadows and reflections.

In analyzing the query image, the system according the invention extracts the static characteristics which are used to eliminate records from further consideration. In a separate and independent process, the invention determines the perspective of the pill in the query image. From the remaining possible match records, the virtual 3D model is manipulated to provide a perspective-adjusted 3d model. In other words, the step of generating a perspective-adjusted 3D model is performed on the match records selected in the first comparing step.

While certain details have been shown and described with respect to hardware, system, and process steps, it should be understood that other options and variations may be incorporated within the spirit of the invention. Various storage devices, computer systems, software applications and telecommunications links may be used. The query images can be captured by a variety of devices and communicated to the CPU by all current and future telecommunications means.

The elements shown in FIGS. 2A, 3A-3C may be implemented in various forms of hardware, software or combinations thereof. Preferably, these elements are implemented in software on one or more appropriately programmed general-purpose digital computers having a processor and memory and input/output interfaces.

Implementations of the present principles can take the form of an entirely hardware embodiment, an entirely software embodiment or an embodiment including both hardware and software elements. Certain aspects of the present invention involving data and image processing, virtual 3D modeling and sorting, comparing and identification steps are implemented in software, which includes but is not limited to firmware, resident software, microcode, etc.

The present principles may be implemented and can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Having described preferred embodiments for processes, apparatus and systems used therein for pill identification (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for identifying a pill comprising the steps of:
storing a pharmaceutical database on an electronic storage device including a virtual 3D model of each pharmaceutical within the database;
transmitting a simple 2D image of a pill to a central processing unit (CPU) that is operatively coupled to the pharmaceutical database;
determining the perspective of the 2D image; and
generating an image of the virtual 3D model from a perspective that matches the perspective of the 2D image.

2. The method of claim 1, wherein the pharmaceutical database includes a plurality of records of known pharmaceuticals, each record contains (i) a virtual 3D model, (ii) static characteristics comprising color, shape and alphanumeric characters of the pharmaceutical, and (iii) medical and safety data.

3. The method of claim 2, wherein the simple 2D image comprises an image taken at a remote field location under ambient lighting conditions with a commercially available digital camera in the absence of spectrally modified lighting other than the camera's flash.

4. The method of claim 3, wherein the transmitting step comprises transmitting simple 2D query image via a wireless cellular telephone network to the CPU, wherein the CPU contains a set of instructions for performing data and image processing, and comparing functions.

5. The method of claim 2, wherein prior to said generating step, the method further includes:
analyzing the simple 2D image to identity one of the color, shape or alphanumeric characters of the imaged pill, wherein the simple 2D image comprises a 2D query image.

6. The method of claim 5, wherein following said analyzing step and prior to said generating step, the method further includes:
comparing one of the identified color, shape or alphanumeric characters to the static characteristics in the database to divide the records into a no-match group and a matched group, whereby only records in the matched group will be eligible for the generating step.

7. The method of claim 6, wherein said generating step includes retrieving a virtual 3D model from a record in the matched group and generating a perspective-adjusted 3D model.

8. The method of claim 7, wherein said generating step includes rendering a 2D matching image of the perspective-adjusted 3D model and comparing the 2D matching image to the 2D query image.

9. The method of claim 6, wherein following said generating and comparing steps, the method includes:
identifying the pill as a known pharmaceutical and transmitting medical and safety data for that pharmaceutical back to the source of the query.

10. A system for identifying a pill comprising:
an electronic storage device containing a pharmaceutical database including a virtual 3D model of each pharmaceutical in the database;
a central processing unit (CPU) operatively coupled to said electronic storage device;
a set of instructions for programming the CPU to perform data and image processing in response to a database query; and
an image generating module that generates an image of a 3D model, wherein the selection of the 3D model is based on said data processing results and the image type is based on said image processing result.

11. The system of claim 10, further comprising a simple query image of a pill requiring identification and a telecommunications network for transmitting the query image to the CPU.

12. The system of claim 11, wherein the pharmaceutical database includes a plurality of records of known pharmaceuticals, each record contains (i) a link to a virtual 3D model, (ii) static characteristics comprising color, shape and alphanumeric characters of the pharmaceutical, and (iii) medical and safety data.

13. The system of claim 12, wherein the image generating module contains a set of instructions for manipulating the 3D model which is capable of showing the 3D model in any orientation and at a range of scales.

14. The system of claim 13, wherein the CPU obtains perspective and scale data from the query image and the image generating module orients the 3D model based on the perspective data to obtain the same perspective as the query image, wherein the oriented 3D model is defined as a perspective-adjusted 3D model.

15. The system of claim 14, wherein the perspective data from the query image is recorded via a coordinate system and transferred to the 3D model.

16. The system of claim 15, wherein the scale data is obtained from a reference object in the query image.

17. The system of claim 16, further including a reference library coupled to the image generating module, wherein the reference library contains 3D models of common objects used to scale the perspective-adjusted 3D model.

* * * * *